United States Patent
Henke

(10) Patent No.: US 12,121,372 B2
(45) Date of Patent: *Oct. 22, 2024

(54) COMPOSITE PACKAGING FACILITATING AN ASEPTIC PRESENTATION OF MEDICINAL PRODUCTS

(71) Applicant: Aesculap AG, Tuttlingen (DE)

(72) Inventor: Matthias Henke, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/453,806

(22) Filed: Aug. 22, 2023

(65) Prior Publication Data

US 2023/0390017 A1 Dec. 7, 2023

Related U.S. Application Data

(63) Continuation of application No. 17/782,437, filed as application No. PCT/EP2020/084340 on Dec. 2, 2020, now Pat. No. 11,771,515.

(30) Foreign Application Priority Data

Dec. 4, 2019 (DE) .................. 10 2019 133 076.9

(51) Int. Cl.
*A61B 50/30* (2016.01)
*A61F 2/00* (2006.01)

(52) U.S. Cl.
CPC ............ *A61B 50/30* (2016.02); *A61F 2/0095* (2013.01); *A61B 2050/3006* (2016.02)

(58) Field of Classification Search
CPC .... A61B 50/30; A61B 2050/3006; A61F 2/0095
USPC .................................................. 206/363, 438
See application file for complete search history.

(56) References Cited

U.S. PATENT DOCUMENTS

| | | |
|---|---|---|
| 3,620,439 A | 11/1971 | Morse et al. |
| 3,727,750 A | 4/1973 | Petter |
| 3,773,248 A | 11/1973 | Cecil et al. |
| 5,993,755 A | 11/1999 | Andersen |
| 8,302,776 B2 | 11/2012 | Lien |
| 9,498,317 B2 | 11/2016 | Gautam et al. |

(Continued)

FOREIGN PATENT DOCUMENTS

| | | |
|---|---|---|
| CN | 205658986 U | 10/2016 |
| CN | 107054875 A | 8/2017 |

(Continued)

OTHER PUBLICATIONS

Office Action received in Chinese Application No. 202080083832.8 dated Apr. 21, 2023, with translation, 10 pages.

(Continued)

*Primary Examiner* — Jacob K Ackun
(74) *Attorney, Agent, or Firm* — Christopher A. Rothe; CM Law

(57) ABSTRACT

A sterile packaging for sterile medicinal products, in particular implants, forms at least one, or in case of a multiple sterile packaging, at least one first sterile barrier and an outer second sterile barrier, separate and independent from the first sterile barrier, and which is accommodated in an outer packaging. The outer packaging is made of a composite material that includes cardboard and at least one coating or film, and is designed and intended to form the second sterile barrier of the sterile packaging.

12 Claims, 3 Drawing Sheets

(56) References Cited

U.S. PATENT DOCUMENTS

| | | |
|---|---|---|
| 2002/0098139 A1 | 7/2002 | Sparks |
| 2006/0071061 A1 | 4/2006 | Velazquez et al. |
| 2009/0054971 A1 | 2/2009 | Mitsunaga et al. |
| 2009/0236253 A1 | 9/2009 | Merckle et al. |
| 2013/0008818 A1 | 1/2013 | Ahag et al. |
| 2013/0233736 A1 | 9/2013 | Hess et al. |
| 2014/0346072 A1 | 11/2014 | Jacobson |
| 2017/0224430 A1 | 8/2017 | Doering |
| 2019/0060050 A1 | 2/2019 | Barnell |
| 2019/0110879 A1 | 4/2019 | Camp et al. |
| 2019/0274809 A1 | 9/2019 | Kapec et al. |
| 2019/0359376 A1 | 11/2019 | Bethune-Bates |
| 2022/0185565 A1 | 6/2022 | Rivera et al. |

FOREIGN PATENT DOCUMENTS

| | | |
|---|---|---|
| DE | 19603476 A1 | 8/1996 |
| DE | 20106402 U1 | 7/2001 |
| EP | 0127466 A2 | 12/1984 |
| EP | 3357444 A1 | 8/2018 |
| GB | 1264975 A | 2/1972 |
| JP | 2013516207 A | 5/2013 |
| JP | 2014508552 A | 4/2014 |
| WO | 2006109668 A1 | 10/2006 |

OTHER PUBLICATIONS

Office Action received in Chinese Application No. 202080083832.8 dated Dec. 30, 2022, with translation, 12 pages.

Search Report received in Chinese Application No. 202080083832.8 dated Apr. 21, 2023, with translation, 4 pages.

Search Report received in Chinese Application No. 2020800838328 dated Dec. 26, 2022, with translation, 4 pages.

Search Report received in German Application No. 10 2019 133 076.9 dated Sep. 21, 2020, with translation, 12 pages.

Search Report received in International Application No. PCT/EP2020/084340 dated Mar. 16, 2021, with translation, 6 pages.

Written Opinion received in International Application No. PCT/EP2020/084340 dated Mar. 16, 2021, with translation, 14 pages.

Notice of Allowance received in Japanese Application No. 2022-533536 dated Jan. 30, 2024, with translation, 2 pages.

COMPOSITE PACKAGING FACILITATING AN ASEPTIC PRESENTATION OF MEDICINAL PRODUCTS

CROSS-REFERENCES TO RELATED APPLICATIONS

This application is a continuation of U.S. application Ser. No. 17/782,437, filed Jun. 3, 2022, which is the United States national stage entry of International Application No. PCT/EP2020/084340, filed Dec. 2, 2020, and which claims priority to German Application No. 10 2019 133 076.9, filed Dec. 4, 2019. The contents of U.S. application Ser. No. 17/782,437, International Application No. PCT/EP2020/084340, and German Application No. 10 2019 133 076.9 are incorporated by reference herein in their entireties.

FIELD

The present disclosure relates to a sterile packaging with preferably an inner, first sterile barrier and an (obligatory) outer, second sterile barrier, which is formed separately and independently from the possibly existing first sterile barrier, for adequate packaging of sterile medical devices, in particular of implants.

BACKGROUND

Medical devices, such as implants, have to be stored in appropriate packaging that prevents contamination by microorganisms until they are used. In general, certain official standards apply to the packaging of medical devices or sterile goods, such as DIN EN ISO 11607 Part 1 and Part 2 and EN 868 2-10, whose requirements have to be met by manufacturers of medical devices and also by healthcare facilities, such as hospitals, in order to ensure adequate and at the same time safe packaging that is adapted to the respective medical device. For example, DIN EN ISO 11607 Part 1 describes the general requirements for materials, sterile barrier systems, and packaging systems.

When selecting the right packaging, several aspects play a decisive role, such as the nature of the medical device to be packaged, the requirements of the users, structural conditions, and transport logistics. However, a corresponding user-friendliness and safety aspects are also of great importance. For example, packaging has to ensure easy filling with the product and germ-tight sealing, while at the same time being robust enough to prevent damage. Appropriate labeling of the packaging or of the contents and sterilization of the packaging also have to be possible. Since the loss of sterility of a medical device depends less on the storage period than on external influences and impacts during transport and storage, the packaging of a medical device should also be selected with regard to the transport and storage conditions of the respective medical device. For example, repeated handling of clear packaging may cause breakage of the material, loosening of the seal seam, formation of channels, or perforations.

Implants such as knee or hip implants are nowadays usually packaged in a double sterile way. This means that the respective implant is packaged in two successive blisters, peel pouches, a combination of both, or something similar to enable aseptic/germ-free presentation in the operating room. In practice, correct aseptic presentation of double sterile-packaged medical devices during surgery requires two operating room nurses in addition to the physician who ultimately inserts the medical device into the patient or uses it during the course of surgery. One of the two operating room nurses assumes the 'non-sterile role', i.e. the opening of an existing outer packaging in which the double-sterile-packaged medical device is contained and the opening of the outer blister, peel pouch, etc., which is formed as a second sterile barrier, while the other one of the two operating room nurses assumes the 'sterile role' and is responsible for the correct opening of the inner blister, peel pouch, etc., which is formed as the first sterile barrier.

However, simple sterile packaging is also sufficient for certain medical products, such as tissue adhesives, but also disposable scalpels or some products used in spinal surgery.

So-called composite packaging is now used almost throughout the whole food packaging sector. Composite packaging is made of bonded/composite materials, i.e. they consist of two or more materials bonded together that have different material properties than the individual material components and even exceed the properties of the individual material components. Since a single material cannot offer all the desired properties, different materials are combined to form a composite that has the desired properties and at the same time meets the requirements for packaging in the food industry.

The most commonly known example of composite packaging in the food industry is beverage cartons or, respectively, disposable packaging for beverages or liquid foods. They consist of cardboard and plastic, and often a thin layer of aluminum, which are bonded together over the entire surface and cannot be separated by hand. Such a structure protects against light and oxygen and in this way suppresses or respectively slows down oxidation processes and the destruction of vitamins and aromas of the packaged food outside the cold chain.

In view of the extensive advantages that composite packaging can offer, depending on their composition, the use of composite packaging or composite materials also appears to make sense in the packaging of sterile medical devices, and in particular for implants, in order to meet the numerous requirements placed on medical device packaging in an efficient manner.

A currently common packaging solution from the prior art is double sterile-barrier packaging of medical devices. Such sterile packaging is used by the majority of medical device manufacturers and consist of an inner, first sterile barrier and an outer, second sterile barrier, wherein blisters, peel pouches, etc. are used to form/create both sterile barriers. That is, a sterile medical device to be packaged is placed in an inner blister, peel pouch, etc. formed as a first sterile barrier. This inner blister, peel pouch, etc. is in turn inserted into an outer blister, peel pouch, etc. formed as a second sterile barrier. This outer blister, peel pouch etc., which contains the inner blister, peel pouch, etc. and the sterile medical device located inside, is then placed in an outer carton, which may be additionally padded for better protection during transport. Finally, the outer carton may also be surrounded by cellophane for protection.

In order to present such a double sterile-packed medical device aseptically during an operation, both a 'non-sterile operating room nurse' and a 'sterile operating room nurse' are required, as already mentioned above. The 'non-sterile operating room nurse' first removes the cellophane surrounding the package, if present, in a non-sterile area during the operation and opens or respectively unfolds the package, thus presenting the double sterile-packaged medical device. The 'non-sterile operating room nurse' then removes, from the outer carton, the double sterile-packaged medical device or, more precisely, the outer blister, peel pouch, etc., formed as a second sterile barrier, containing the inner blister, peel pouch, etc., formed as a first sterile barrier, and the sterile medical device contained therein. Now the outer blister, peel pouch, etc. formed as the second sterile barrier is opened aseptically by the 'non-sterile operating room nurse' and the inner blister, peel pouch, etc. formed as the first sterile barrier is handed over/presented to the 'sterile operating room nurse', who is located in a sterile area. The inner blister, peel pouch, etc. formed as the first sterile barrier including the sterile medical device contained therein, is then removed by the 'sterile operating room nurse' from the opened outer blister, peel pouch, etc. formed as the second sterile barrier and opened in the sterile area of the operating room. The sterile medical device inside is then handed to the operating physician and used on and/or in the patient.

When opening the outer blister, peel pouch, etc. formed as the second sterile barrier, the 'non-sterile operating room nurse' has to ensure that the inner blister, peel pouch, etc. formed as the first sterile barrier, is not rendered non-sterile by inadequate handling. In addition, both the 'non-sterile nurse' and the 'sterile nurse' have to pay close attention during all the steps described above that the medical device remains sterile and does not fall to the floor or becomes damaged in any other way, since an unsterile and/or damaged medical device must/should no longer be used on a patient. Furthermore, the common packaging, such as peel pouches, is tightly sealed, which is why they are very difficult to open or can only be opened by jerking. The operating room nurses therefore have to exert a relatively large amount of force to open them. These circumstances and the often existing time pressure during operations often lead to errors in the aseptic presentation of medical devices or, respectively, to an undesired complication of the aseptic presentation of medical devices.

Double sterile-packaged medical devices according to the prior art also have a rather large overall packaging effort and take up comparatively much packaging volume.

But even in the case of a single sterile barrier, the sterile-packaged medical device is packed in an additional redistribution/outer packaging, preferably made of cardboard, which increases the overall packaging effort.

Therefore, there is a need for single and double sterile-barrier packaging for sterile medical devices, in particular for implants, which allows a simpler and less complicated aseptic presentation of sterile medical devices during surgery, and at the same time require significantly less packaging volume and generate less packaging waste than comparable sterile packaging of the prior art.

SUMMARY

In view of the problems described above, it is therefore a fundamental object of the present invention to provide sterile packaging with a single or double sterile barrier for sterile medical devices, in particular implants, which, despite additional outer packaging, saves overall packaging material and/or packaging effort and thus significantly reduces packaging waste on the one hand and the costs incurred by the manufacturer for the packaging of medical devices and the packaging process on the other hand.

In this context, a further object of the present invention is to simplify the aseptic presentation of packaged, sterile medical devices using a more practical opening mechanism and to avoid complicated unpacking of the medical device. At the same time, the present invention can reduce the individual unpacking steps of the 'non-sterile operating room nurse', which minimizes the workload and results in saved time during an operation. Furthermore, the reduction of the unpacking steps and the simplified opening mechanism also reduces the risk of the medical device being dropped, damaged, or generally rendered unsterile during the unpacking process.

Accordingly, the core idea of the present invention is not only to provide a sterile packaging with an (inner) first sterile barrier and preferably an (outer) second sterile barrier, which is contained in a corresponding outer packaging, as is proposed in the prior art, but furthermore to combine the properties and functions of the respective, if applicable, outer, second sterile barrier (if present) and the outer packaging using a special structure of the outer packaging.

In other words, the outer packaging of the sterile packaging is designed as composite packaging, for example in the sense of a beverage carton. In this way, several functions can be realized by the outer packaging and, in addition, the respective (only) existing, in the case of a double packaging the outer, second sterile barrier can be formed in the outer packaging. This simplifies the aseptic presentation of the medical device contained in the sterile packaging during an operation on the one hand and also reduces the packaging volume and packaging material.

Specifically, a sterile packaging for sterile medical devices, in particular implants, is provided which comprises an (inner) first sterile barrier and, if applicable, an outer, second sterile barrier which is separate from and independent of the first sterile barrier and which is contained in an outer packaging. According to the invention, the outer packaging is made of a composite material, inter alia of a cardboard and at least one coating or film, and is configured and provided to form the single and, in the case of a double sterile packaging, the outer, second sterile barrier of the sterile packaging. In addition, the sterile packaging according to the present invention can also be used for other sterile products.

According to a further aspect of the invention, it is advantageous if the outer packaging is additionally surrounded by cellophane. Compared to other plastics, cellophane is produced from renewable rather than fossil raw materials and is compostable. This makes cellophane generally more environmentally friendly than conventional films used for packaging. Although cellophane is on the one hand waterproof, it also has the advantage of allowing water to pass through as vapor molecules, thus avoiding the accumulation of water within the sterile packaging. In addition to its transparency, it also has excellent printing performance and can be printed with ordinary ink, making it well suited as a packaging material in general or as an additional coating for packaging, respectively.

In order to ensure a robust outer (second) sterile barrier that meets the requirements for the packaging of medical devices, the composite material of the outer packaging according to another aspect of the invention consists of a multi-layer composite, for example in the sense of a beverage carton, made of cardboard and a plastic film, in particular polyethylene foil. The cardboard gives shape and stability to the composite material and also provides a smooth surface for printing on the sterile packaging. In the case of double sterile packaging, the polyethylene foil protects the inner packaging formed as the first sterile barrier and the medical device located inside it from moisture. According to a further aspect of the present invention, the composite material of the outer packaging may also comprise a multi-layer composite made of cardboard, a plastic film, in particular polyethylene foil, and an aluminum foil. In this case, the polyethylene foil serves not only as protection against moisture but also as an adherent layer between the cardboard and the aluminum foil. The purpose of the aluminum foil is to protect the contents, i.e. the medical device in the outer packaging or, if applicable, in the inner packaging formed as the first sterile barrier, from external influences such as extreme temperatures. The sterile packaging can be specifically configured in such a way that the multi-layer composite consists, from the inside to the outside, of the cardboard, two layers of polyethylene foil, a layer of aluminum foil followed by another layer of polyethylene foil, a layer of paper and an outer layer of polyethylene foil. The outermost polyethylene foil additionally protects the cardboard from soaking and increases the barrier properties of the multi-layer composite. Alternatively, the multi-layer composite may also have a different structure or respectively a different arrangement and may be designed variably depending on its function.

A further embodiment of the present invention is the integration of possibly also gas-permeable areas in the multi-layer composite, in order to enable, in addition to a common sterilization method such as gamma sterilization, other common methods such as sterilization with ethylene oxide.

In order to be able to open the outer packaging and to remove the sterile medical device stored therein, which may be located in the inner packaging formed as a first sterile barrier, the outer packaging possibly formed as a second sterile barrier of the sterile packaging has a predetermined breaking point according to one aspect of the invention. According to a further aspect of the invention, the predetermined breaking point is located at an upper third of the outer packaging possibly formed as a second sterile barrier of the sterile packaging. In this regard, according to yet another aspect of the invention, the predetermined breaking point is perforated. This ensures that the 'non-sterile operating room nurse' can open or bend the outer packaging comparatively easily and without complications. Such an opening mechanism of the outer packaging simultaneously reduces the risk that the sterile medical device, which may be in the inner packaging formed as the first sterile barrier, falls to the floor and is damaged and can therefore no longer be used.

In order to prevent the perforated predetermined breaking point from compromising the intact single or double sterile barrier, the perforation must not include all layers. According to one aspect of the invention, therefore, with the exception of the innermost layer of the multi-layer composite of the composite material of the outer packaging, all layers of the multi-layer composite are perforated. Alternatively, fewer or only certain layers of the multi-layer composite may be perforated. In other words, more layers of the multi-layer composite than just the innermost layer may be free of perforation.

According to another aspect of the invention, the predetermined breaking point may additionally be provided with a pull tab/peel-off tab. A pull tab/peel-off tab incorporated into the outer packaging in addition to the predetermined breaking point provides an efficient alternative for easier and less complicated opening of the sterile packaging.

Finally, in the case of a double sterile packaging, the inner packaging configured as a first sterile barrier, in which at least one sterile medical device is contained, protrudes according to a further aspect of the invention when the outer packaging formed as the second sterile barrier is opened/bent. That is, an upper portion of the inner packaging formed as the first sterile barrier projects above the opened/bent outer packaging configured as a second sterile barrier. In this way, the inner packaging formed as the first sterile barrier, can be removed simply and easily by the 'sterile operating room nurse' without having to reach into the outer packaging.

At this point, it should be pointed out explicitly that the above aspects individually as well as in any combination with each other can solve the stated object and are therefore intended to be claimable individually or in any combination within the scope of this application.

BRIEF DESCRIPTION OF THE DRAWING FIGURES

The present invention is described in more detail below by using preferred configuration examples with reference to the accompanying drawings. The following is shown:

DETAILED DESCRIPTION

Configuration examples of the present disclosure are described below on the basis of the associated figures. Identical or functionally equivalent features are provided with the same reference signs in the individual figures.

Figure 1:
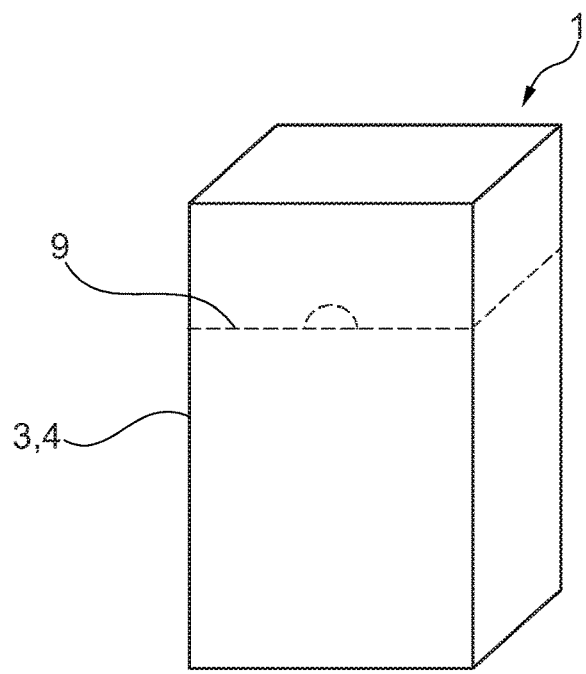
FIG. 1 shows a representation illustrating a sterile packaging for sterile medical devices according to a first configuration example of the present disclosure.

FIG. 1 shows an unopened sterile packaging 1 for sterile medical devices, in particular for implants, which has an inner, first sterile barrier 2, not shown in FIG. 1, and an outer, second sterile barrier 3 formed separately and independent of the first sterile barrier 2, and which is contained in an outer packaging 4. The outer packaging 4 consists of a composite material not shown in detail in FIG. 1, including a cardboard 5 and at least one coating or film, and is configured and provided to form the second sterile barrier 3 of the sterile packaging 1.

Furthermore, the outer packaging 4 formed as the second sterile barrier 3 of the sterile packaging 1 has a predetermined breaking point 9, which serves to open the outer packaging 4. Since the outer packaging 4 in FIG. 1 is still unopened/closed, both the predetermined breaking point 9 and the outer, second sterile barrier 3 are still intact. The predetermined breaking point 9 is arranged at an upper third of the outer packaging 4 formed as the second sterile barrier 3 of the sterile packaging 1, in order to facilitate removal of an inner packaging 11 formed as the first sterile barrier 2, which is located in the outer packaging 4 formed as the second sterile barrier 3. According to the first configuration example in FIG. 1, the predetermined breaking point 9 is achieved by perforation of the outer packaging 4. In order not to endanger the outer, second sterile barrier 3 in the case of pre-perforation and to ensure the sterility of the medical device contained in the outer packaging 4, the pre-perforation must not include all layers. That is, at least the innermost layer of the composite material is not perforated.

Therefore, according to the present invention, with the exception of the innermost layer of the multi-layer composite of the composite material of the outer packaging 4, all layers of the multi-layer composite are perforated. Alternatively, however, fewer or only certain layers of the multi-layer composite may be perforated. In other words, more layers of the multi-layer composite than just the innermost layer may be free of perforation.

In addition, the sterile packaging 1 may be surrounded/sheathed by cellophane, which is not further shown in FIG. 1, which additionally protects the sterile packaging 1 from moisture due to its water-repellent properties and prevents water from accumulating inside the sterile packaging 1. In practice, a 'non-sterile operating room nurse' removes the cellophane that may surround the outer packaging 4 and opens the outer packaging 4 formed as the second sterile barrier 3, by bending/breaking open the outer packaging 4 at the predetermined breaking point 9. In this way, the outer, second sterile barrier 3 is also broken open at the same time.

Figure 2:
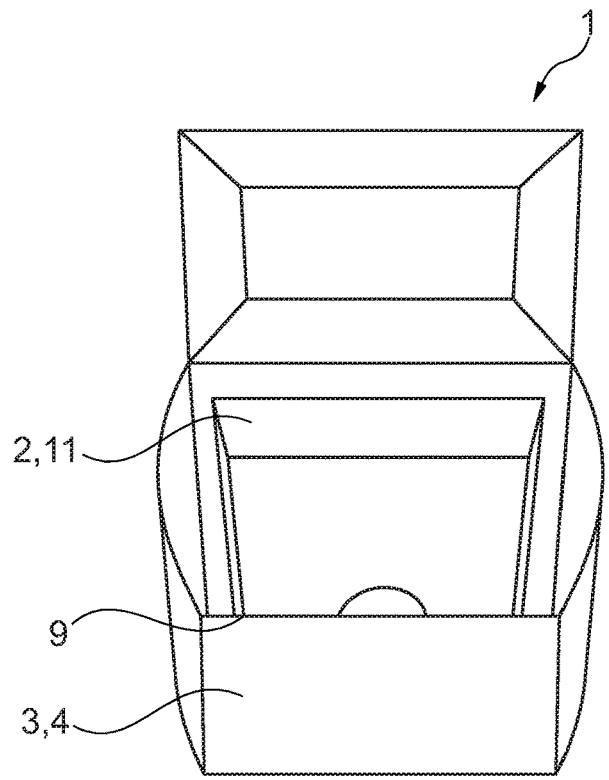
FIG. 2 shows a top view of an opened sterile packaging for sterile medical devices according to the first configuration example of the present disclosure.

In FIG. 2, the sterile packaging 1 according to the first configuration example of the present disclosure of FIG. 1 is shown in an open state from above. By opening or bending the outer packaging 4 formed as the second sterile barrier 3, at the predetermined breaking point 9, the intact inner packaging 11 formed as the first sterile barrier 2, for example in the form of a sterile blister, peel pouch, etc., is exposed and can be removed by the 'sterile operating room nurse'.

Figure 3:
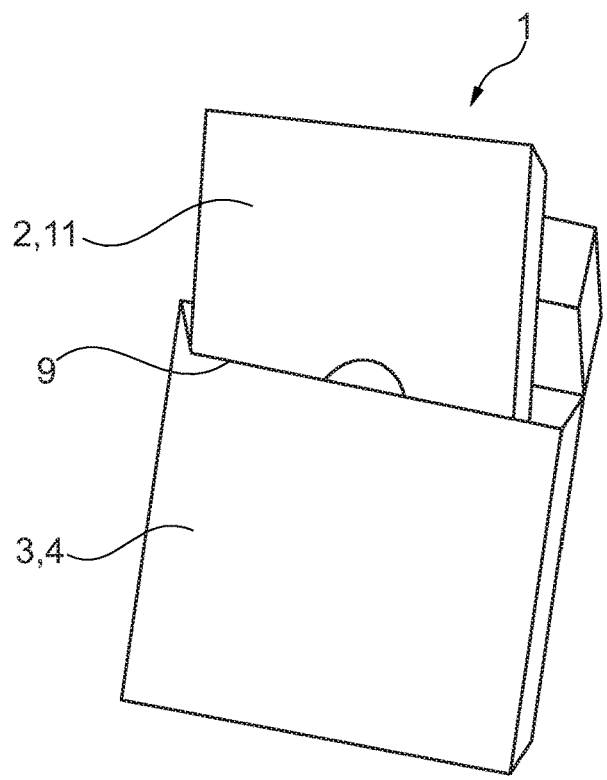
FIG. 3 shows a front view of the opened sterile packaging for sterile medical devices according to the first configuration example of the present disclosure.

FIG. 3 shows the opened sterile packaging 1 according to the first configuration example of the present disclosure from FIG. 2 from the front. From this perspective, it becomes apparent to what extent the arrangement of the predetermined breaking point 9 at an upper third of the outer packaging 4 formed as the second sterile barrier 3 is advantageous for removing the inner packaging 11 formed as the first sterile barrier 2. In order to reduce the packaging volume and thus the production of packaging waste, the inner packaging 11 formed as the first sterile barrier 2 and the outer packaging 4 formed as the second sterile barrier 3 are adapted to each other in terms of size/dimension depending on the medical device being packaged. This means that rather small medical devices, which are contained in an inner packaging 11 formed as the first sterile barrier 2 appropriate for their size, are not contained in a disproportionately large outer packaging 4 formed as the second sterile barrier 3. This ensures that the inner packaging formed as the first sterile barrier 2 protrudes beyond the opened outer packaging 4 formed as the second sterile barrier 3 or, respectively, protrudes beyond the opened outer packaging 4 formed as the second sterile barrier 2. The inner packaging 11 formed as the first sterile barrier 2 can now be easily removed by the 'sterile operating room nurse' due to the existing protrusion and the sterile medical device can be handed to the attending physician after opening the inner packaging 11 formed as the first sterile barrier 2.

Figure 4:
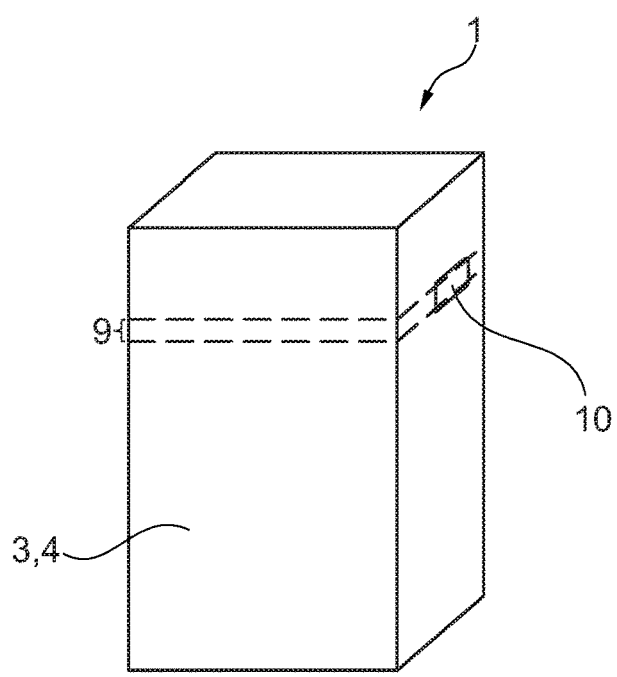
FIG. 4 shows a representation illustrating a sterile packaging for sterile medical devices according to a second configuration example of the present disclosure.

FIG. 4 shows a second configuration example of sterile packaging 1 for medical devices according to the invention. Identical elements and/or components of the first configuration example from FIGS. 1 to 3 are provided with the same reference signs, so that only differences between the first and second configuration examples are discussed below. In this configuration example, the sterile packaging 1 is additionally provided with a pull tab/peel-off tab 10 at the predetermined breaking point 9. In addition to the predetermined breaking point 9, the pull tab/peel-off tab 10 serves as a further possibility to open the sterile packaging 1 more easily than has been possible in the prior art. By pulling on the pull tab/peel-off tab 10, the outer packaging 4 formed as the second sterile barrier 3 can be torn open/opened at the predetermined breaking point 9 without complications and without relatively much force.

Figure 5:
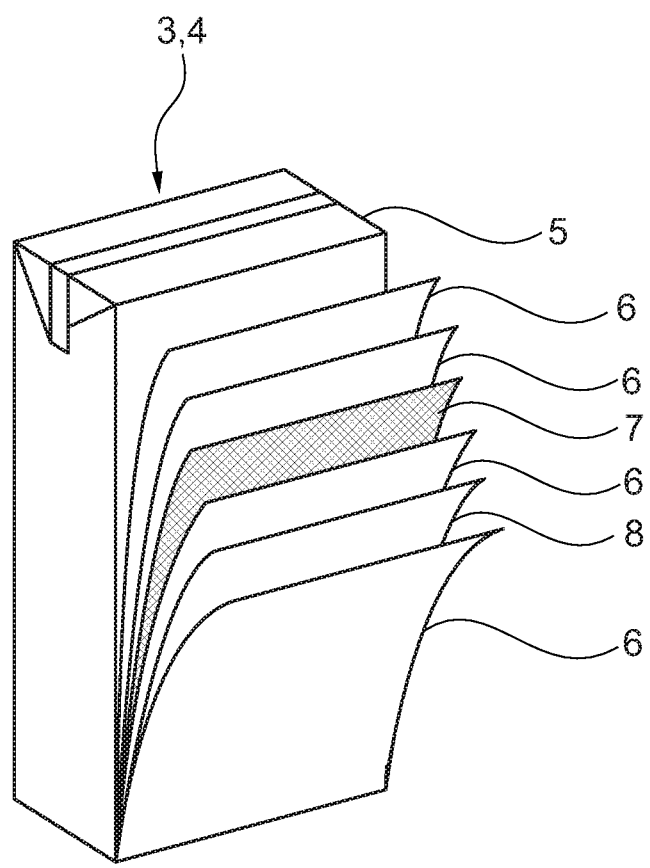
FIG. 5 shows an illustration of a typical structure of an outer packaging of the sterile packaging according to the present disclosure.

FIG. 5 shows a typical structure of an outer packaging 4 of the sterile packaging 1 according to the present disclosure. According to the present invention, the outer packaging 4 is configured as a composite packaging, for example in the manner of a beverage carton, consisting of so-called composite materials. In FIG. 5, the composite material of the outer packaging 4 consists of a multi-layer composite made of cardboard 8, a plastic film 6, in particular polyethylene foil 6, and an aluminum foil 7. However, the composite material of the outer packaging 4 may alternatively also consist only of a multi-layer composite made of cardboard 5 and a plastic film 6, in particular polyethylene foil 6. The individual material components fulfill different functions in this context. The cardboard 8 gives the composite material shape and stability and also provides a smooth surface for printing on the sterile packaging 1. The plastic film or polyethylene foil 6 in turn protects the inner packaging 11 formed as the first sterile barrier 2 and the medical device located therein from moisture and serves as an adherent layer between the cardboard 5 and the aluminum foil 7. The aluminum foil 7 in turn protects the medical device located in the outer packaging 4 in the inner packaging 11 formed as the first sterile barrier 2 from external influences, such as extreme temperatures. For an efficient combination of the individual functions of the material components, the multi-layer composite may consist of two layers of polyethylene foil 6 from the inside to the outside, a layer of aluminum foil 7 followed by another layer of polyethylene foil 6, a layer of paper or cardboard 8 and an outer layer of polyethylene foil 6. Alternatively, the multi-layer composite may have a different structure and may be designed variably depending on its function.

In summary, the invention relates to a sterile packaging 1 for sterile medical devices, in particular implants, which has an inner, first sterile barrier 2 and an outer, second sterile barrier 3, which is separate from and independent of the first sterile barrier 2, and which is contained in an outer packaging 4. According to the invention, the outer packaging 4 of such a sterile packaging 1 consists of a composite material, including a paper/cardboard 8 and at least one coating or film, and is configured and provided to form the second sterile barrier 3 of the sterile packaging 1.

In summary, the invention relates to a sterile packaging for sterile medical devices, in particular implants, which has at least one or, in the case of a multiply sterile packaging, at least an inner, first sterile barrier and an outer, second sterile barrier which is separate from and independent of the first sterile barrier and which is contained in an outer packaging. According to the invention, the outer packaging of such a sterile packaging consists of a composite material, inter alia made of a cardboard and at least one coating or film, and is configured and provided to form the second sterile barrier of the sterile packaging.

The invention claimed is:

1. A sterile packaging for sterile medical devices the sterile packaging comprising:
   an inner packaging comprising a first sterile barrier; and
   an outer packaging comprising a second sterile barrier, the second sterile barrier being separate from and independent of the first sterile barrier,
   the first sterile barrier and the second sterile barrier forming a double sterile packaging,
   the outer packaging comprising a composite material that includes a cardboard and at least one coating or film, the outer packaging configured and provided to form the second sterile barrier, and the inner packaging configured as the first sterile barrier and containing at least one sterile medical device, the inner packaging configured to protrude beyond the outer packaging when the outer packaging is opened.

2. The sterile packaging for sterile medical devices according to claim 1, wherein a part of the outer packaging is configured to be gas-permeable.

3. The sterile packaging for sterile medical devices according to claim 1, wherein the outer packaging is surrounded by cellophane.

4. The sterile packaging for sterile medical devices according to claim 1, wherein the composite material comprises a multi-layer composite made of the cardboard and a plastic film.

5. The sterile packaging for sterile medical devices according to claim 4, wherein the multi-layer composite further comprises an aluminum foil.

6. The sterile packaging for sterile medical devices according to claim 5, wherein the multi-layer composite comprises, from an inside of the multi-layer composite to an outside of the multi-layer composite, a first layer of polyethylene foil, a second layer of polyethylene foil, a layer of the aluminum foil, a third layer of polyethylene foil, the cardboard, and a fourth layer of polyethylene foil.

7. The sterile packaging for sterile medical devices according to claim 1, wherein the outer packaging has a predetermined breaking point.

8. The sterile packaging for sterile medical devices according to claim 7, wherein the predetermined breaking point is located at an upper third of the outer packaging.

9. The sterile packaging for sterile medical devices according to claim 7, wherein the predetermined breaking point is perforated.

10. The sterile packaging for sterile medical devices according to claim 4, wherein at least one layer of the multi-layer composite is not perforated.

11. The sterile packaging for sterile medical devices according to claim 4, wherein all layers of the multi-layer composite are perforated except for an innermost layer of the multi-layer composite.

12. The sterile packaging for sterile medical devices according to claim 7, wherein the predetermined breaking point is provided with a pull tab/peel-off tab.

* * * * *